(12) United States Patent
Wu

(10) Patent No.: US 12,290,632 B1
(45) Date of Patent: May 6, 2025

(54) PORTABLE CHILD ANTI-CHOKING FIRST AID EQUIPMENT

(71) Applicant: Shenzhen Huayuwantuo Technology Co., LTD, Guangdong (CN)

(72) Inventor: Jie Wu, Guangdong (CN)

( * ) Notice: Subject to any disclaimer, the term of this patent is extended or adjusted under 35 U.S.C. 154(b) by 0 days.

(21) Appl. No.: 18/937,637

(22) Filed: Nov. 5, 2024

(30) Foreign Application Priority Data

Oct. 6, 2024 (CN) .......................... 202422405647.4

(51) Int. Cl.
| | | |
|---|---|---|
| *A61M 16/00* | (2006.01) | |
| *A61B 17/24* | (2006.01) | |
| *A61B 17/50* | (2006.01) | |
| *A61M 1/00* | (2006.01) | |
| *A61M 16/20* | (2006.01) | |

(52) U.S. Cl.
CPC ......... *A61M 16/0009* (2014.02); *A61B 17/24* (2013.01); *A61B 17/50* (2013.01); *A61M 16/0075* (2013.01); *A61M 16/208* (2013.01); *A61M 1/67* (2021.05)

(58) Field of Classification Search
CPC ... A61B 17/50; A61M 16/00; A61M 16/0063; A61M 16/06; A61M 16/208; A61M 2202/0208; A61M 16/0075–0084; A61M 16/0009; E03C 1/308; E03D 9/00; F16J 1/00; F16J 1/005; F16J 1/006; F16J 3/00–06

USPC ...................................................... 128/205.19
See application file for complete search history.

(56) References Cited

U.S. PATENT DOCUMENTS

| | | | | |
|---|---|---|---|---|
| 11,478,575 | B1 * | 10/2022 | He | A61M 1/67 |
| 2015/0190158 | A1 * | 7/2015 | Lih | A61M 16/0075 606/106 |
| 2018/0099108 | A1 * | 4/2018 | Baek | A61M 16/0081 |

FOREIGN PATENT DOCUMENTS

CN 118141489 A * 6/2024 ............. A61B 17/50

* cited by examiner

*Primary Examiner* — Elliot S Ruddie

(57) ABSTRACT

The invention relates to the technical field of first aid equipment, and discloses a portable child anti-choking first aid equipment, including a face mask, an air cylinder grip, an outflow one-way valve, an inlet one-way valve, and also including a folding airbag. The foldable airbag is mounted between the mask and the air cylinder grip. When the folded airbag is pulled up, the gas is discharged and the foreign matter is sucked out, and the gas brief grip is pulled upward to drive the folded airbag to pull up. When the air simple grip is pressed downward, the outflow check valve opens and the inlet check valve closes, discharging the gas inside the folded airbag. When folded, the foldable anti-asphyxiation first aid equipment is more than three times smaller than portable first aid equipment on the market, making it easy for parents or child caregivers to carry in their bags.

6 Claims, 2 Drawing Sheets

PORTABLE CHILD ANTI-CHOKING FIRST AID EQUIPMENT

TECHNICAL FIELD

The present invention relates to the technical field of first aid equipment, specifically portable child anti-choking first aid equipment.

BACKGROUND OF THE PRESENT INVENTION

Choking is usually caused by the obstruction of the airway by food or foreign objects, resulting in oxygen not being able to enter the lungs. Children are more prone to choking due to their physiological structure and behavioral habits (e.g., eating quickly, eating while playing, etc.).

Commercially available anti-choking first aid equipment is not easy to carry around. In the event of an emergency, going to a storage place or getting it from the car delays important first aid and may lead to life-threatening situations. For this reason, we propose the portable child anti-choking first aid equipment.

SUMMARY OF PRESENT INVENTION

The purpose of the present invention is to provide portable child anti-choking first aid equipment, in order to solve the above background technology proposed in the anti-choking first-aid equipment on the market is not easy to carry around. In the event of an emergency, going to a storage place or a car to get it delays important first aid time and may lead to life-threatening problems.

In order to realize the above purpose, the present invention provides the following technical solution: a portable child anti-choking first aid equipment, including a face mask, an air cylinder grip, an outflow one-way valve, an inlet one-way valve, and also including a folding airbag. The folding airbag is installed between the mask and the air cylinder grip, and the folding airbag discharges gas to suck out foreign matter when it is pulled up.

Preferably, the folding airbag includes an airbag hard rubber holder and a soft rubber airbag. A number of soft rubber airbags are provided at equal intervals between the mask and the air cylinder grip. The plurality of soft rubber airbags are connected at the gap by the airbag hard rubber holder. The inner diameter of the plurality of soft rubber air bladders increases from top to bottom.

Preferably, the folded airbags are fitted with a cylinder grip bracket at the top of the interior of the folded airbags. An air outlet check valve is assembled inside the air cylinder grip bracket. The top of the folded airbag is threadedly connected to the air cylinder grip by means of a screw.

Preferably, an air cylinder holder is mounted at the bottom end of the interior of the folded airbag. The inlet check valve is assembled inside the air cylinder holder. The bottom of the folded airbag is threadedly connected to the air cylinder face shell by screws, and the bottom of the air cylinder face shell is connected to the mask.

Preferably, the surface of the air cylinder grip is provided with equally spaced exhaust holes.

Compared with the prior art, the beneficial effects of the present invention are:

First, the present invention provides a folded airbag between the air cylinder grip and the face shell. A number of soft rubber air bladders are provided longitudinally inside the folded air bladder. The inner diameters of the plurality of soft rubber air bladders increase in order from top to bottom, and adjacent soft rubber air bladders are connected by an airbag hard rubber holder. When the folded airbag is pulled up, the inner space of the soft rubber airbags and the hard rubber support of the airbag becomes larger to form negative pressure and suck out the foreign matter. When a dangerous situation occurs, insert the mask immediately suction out the foreign body, greatly saving the time to take the equipment and discharge the gas, and the success rate of life-saving is multiplied.

Second, the invention in the folding airbag internal top set out of one-way valve. In the folding airbag at the bottom of the internal set inlet one-way valve. When the gas simple grip is pressed downward, the outflow check valve opens, and the inlet check valve closes, discharging the gas inside the folded airbag. When the air simple grip is pulled upward, the outlet check valve closes and the inlet check valve opens to suck out the foreign matter. Through the design of two groups of one-way valve actual use of better efficiency, better results.

Third, the invention folding anti-asphyxiation first aid equipment folded volume than the market portable first aid equipment more than three times smaller, easy for parents or children caregivers to carry in the bag. When a dangerous situation occurs, insert the mask immediately suction out the foreign body in the trachea, thus greatly saving the time to take the equipment and discharge gas, the success rate of life-saving multiplied. Foldable small size portable anti-asphyxiation first aid equipment can save more than two minutes after asphyxiation to take the equipment and more than two seconds to expel gas time, can greatly improve the first aid time after asphyxiation of a foreign body in the trachea, save more lives.

In the figure, 1 refers to mask; 2 refers to air cylinder grip; 3 refers to air cylinder grip bracket; 4 refers to air bag hard rubber bracket; 5 refers to air cylinder bracket; 6 refers to air cylinder face shell; 7 refers to exhaust hole; 8 refers to outgoing one-way valve; 9 refers to soft rubber air bag; 10 refers to inlet one-way valve; 11 refers to screws.

DETAILED DESCRIPTION OF THE EMBODIMENTS

The technical solutions in the embodiments of the present invention will be clearly and completely described below in conjunction with the accompanying drawings in the embodiments of the present invention. Obviously, the described embodiments are only a part of the embodiments of the present invention, and not all of the embodiments. Based on the embodiments in the present invention, all other embodiments obtained by a person of ordinary skill in the art without making creative labor are within the scope of protection of the present invention.

Figure 1:
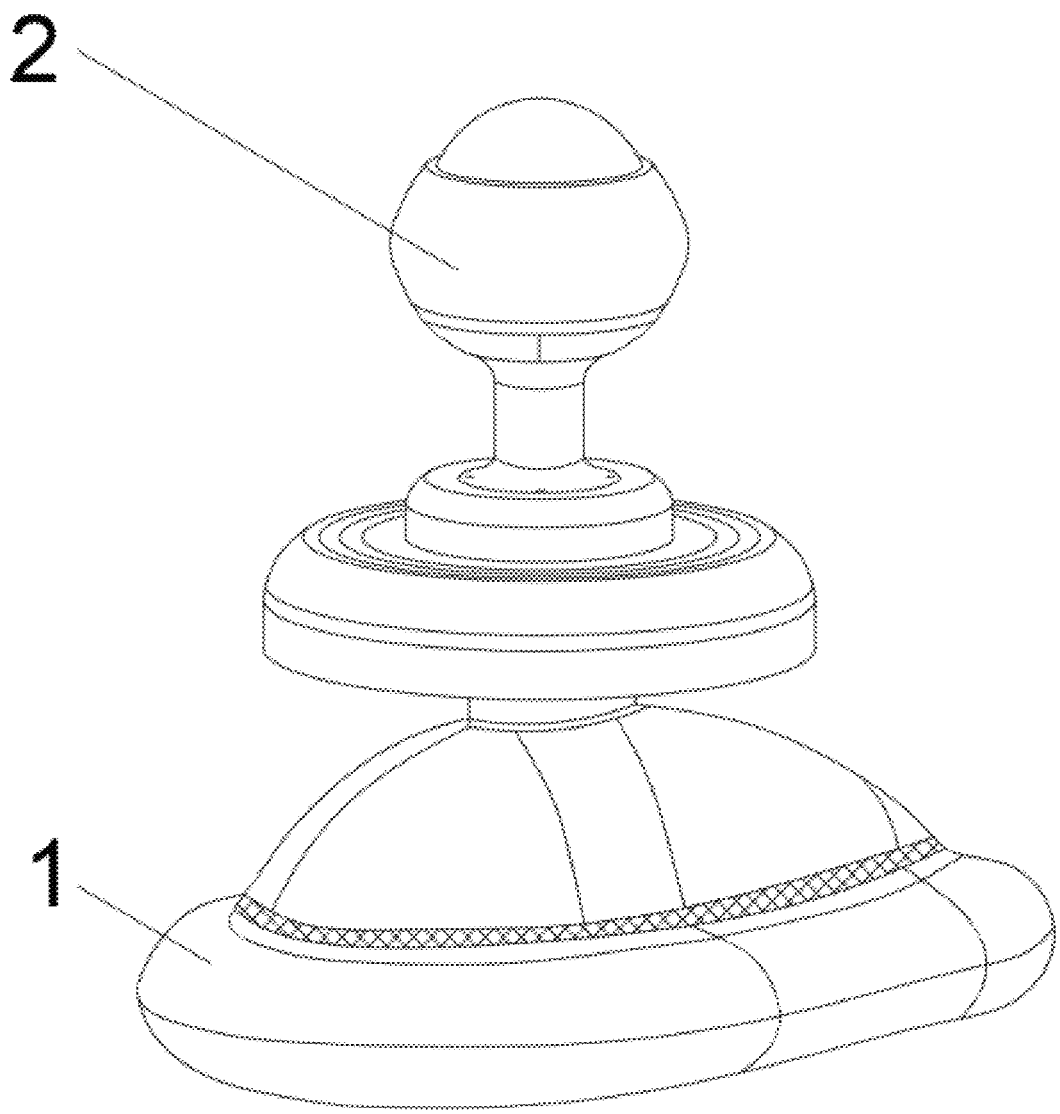
FIG. 1 shows a schematic diagram of the overall structure of the present invention.
Figure 2:
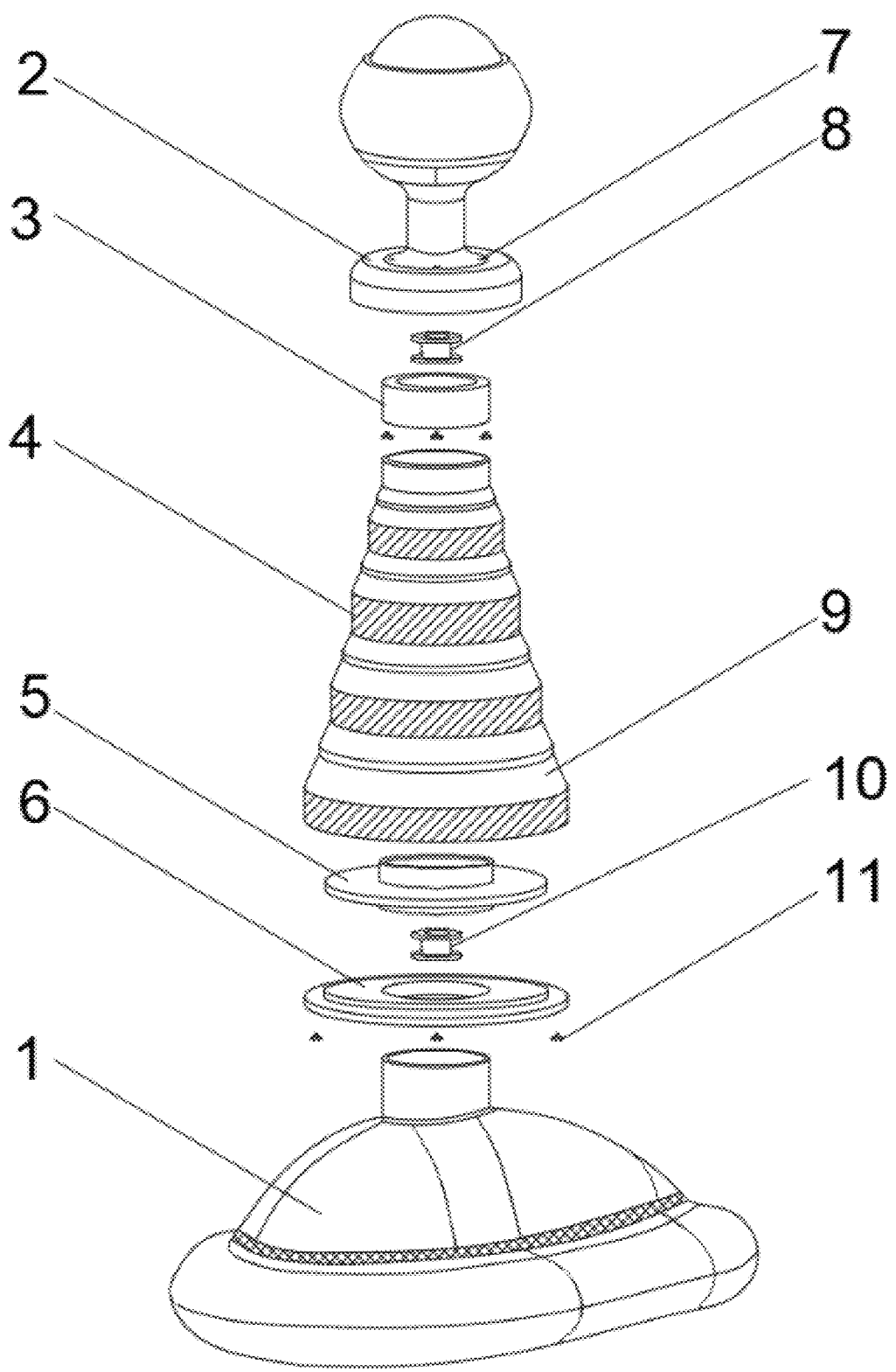
FIG. 2 shows a schematic diagram of the exploded structure of the present invention.

Referring to FIG. 1 and FIG. 2, the portable child anti-choking first aid equipment shown includes a face mask 1, an air cylinder grip 2, an outflow one-way valve 8, an inlet one-way valve 10, and further includes a folding airbag. The foldable airbag is mounted between the mask 1 and the air cylinder grip 2. The folded airbag discharges gas to suck out foreign matter when it is pulled up. The foldable airbag includes an airbag hard rubber holder 4 and a soft rubber airbag 9. A number of soft rubber airbags 9 are provided at equal intervals between the mask 1 and the air cylinder grip 2. A number of soft rubber airbags 9 are connected at the gaps by the airbag hard rubber holder 4. The inner diameters of the plurality of soft rubber airbags 9 increase from top to bottom. At the top end of the interior of the folded airbag, an air cylinder grip holder 3 is mounted, and an air outlet check valve 8 is assembled inside the air cylinder grip holder 3. The top end of the folded airbag is threadedly connected to the air cylinder grip 2 by a screw 11. At the bottom end of the folded airbag, there is a cartridge holder 5, which is equipped with an inlet check valve 10. The bottom end of the folded airbag is connected to a cartridge face shell 6 by screws 11. The bottom end of the cartridge face shell 6 is connected to the mask 1. Equally spaced exhaust holes 7 are provided on the surface of the air cylinder grip 2.

A folded airbag is provided between the air cylinder grip 2 and the mask 1. A longitudinal number of soft rubber airbags 9 are provided inside the folded airbag. the inner diameters of the number of soft rubber airbags 9 increase in order from top to bottom, and adjacent soft rubber airbags 9 are connected by an airbag hard rubber holder 4. When the folded airbag is pulled up, the inner space of the soft rubber airbags 9 and the airbag hard rubber holder 4 becomes larger to form a negative pressure and suck out the foreign matter. When a dangerous situation occurs, inserting the mask 1 immediately sucks out the foreign matter, greatly saving the time for taking the equipment and discharging the gas, and the success rate of saving lives increases exponentially;

In the folding airbag inside the top set out of the one-way valve 8, in the folding airbag inside the bottom set inlet one-way valve 10. Gas simple grip 2 downward pressure, out of the one-way valve 8 open, inlet one-way valve 10 closed, discharge folding airbag internal gas. Air simple grip 2 upward pull, out of one-way valve 8 closed, inlet one-way valve 10 open, suction out of foreign objects. The design of two sets of check valves is more efficient and effective in actual use;

Folding anti-asphyxiation first aid equipment when folded size than the market portable first aid equipment more than three times smaller, easy for parents or child caregivers to carry in the bag. The folded small size portable anti-asphyxiation first aid equipment can save more than two minutes after asphyxiation to fetch the equipment and more than two seconds to expel the gas, which can greatly improve the time of first aid after asphyxiation of a foreign body in the trachea and save more lives.

It should be noted that the present invention is a portable child anti-choking first aid equipment. When a dangerous situation occurs, take out the equipment from the parent or the child caregiver's carry-on bag, set the mask on the child's mouth, pull upward the gas simple grip 2, the gas simple grip 2 pulls the folded airbag pull up, the outgoing one-way valve 8 closes, and the inlet one-way valve 10 opens. Soft rubber airbag 9 and airbag hard rubber bracket 4 internal space becomes bigger to form negative pressure, suck out the foreign body. After the first aid is completed, pressing down on the air simple grip 2 compresses the folded airbag, the outgoing one-way valve 8 opens, the inlet one-way valve 10 closes, and the gas inside the soft rubber airbag 9 and the airbag hard rubber bracket 4 is discharged through the outgoing one-way valve 8 and the exhaust holes 7, and the folding and stowage of the device is completed.

It is to be noted that in this paper, relationship terms such as first and second are used only to distinguish one entity or operation from another, and do not necessarily require or imply the existence of any such actual relationship or order between these entities or operations. Furthermore, the terms "including", "comprising", or any other variant thereof, are intended to cover non-exclusive inclusion, such that a process, method, article, or apparatus comprising a set of elements includes not only those elements, but also other elements not expressly listed, or other elements that are not expressly listed for the purpose of such a process, method, article or apparatus, or other elements that are not expressly listed for the purpose of such a process, method, article or equipment. elements, or also includes elements that are inherent to such process, method, article, or apparatus.

Although embodiments of the present invention have been shown and described, it will be appreciated by those of ordinary skill in the art that a variety of changes, modifications, substitutions, and variations may be made to these embodiments without departing from the principle and spirit of the present invention, the scope of which is limited by the appended claims and their equivalents.

The invention claimed is:

1. A portable child anti-choking first aid equipment, comprising a mask (1), an air cylinder grip (2), an outgoing one-way valve (8), an inlet one-way valve (10), and a folding airbag, wherein the folding airbag is coupled to the mask (1), wherein the folding airbag is arranged between the mask and air cylinder grip (2), wherein the folding airbag is configured, when expanded, to generate a negative pressure to suction out a foreign body from a subject; wherein the folding airbag comprises a plurality of airbag hard rubber supports (4) and a plurality of soft rubber airbags (9), wherein the plurality of soft rubber airbags (9) and the plurality of airbag hard rubber supports (4) are provided alternatingly at equal distances between the mask (1) and the air cylinder grip (2).

2. The portable child anti-choking first aid equipment according to claim 1, characterized in that inner diameters of the plurality of soft rubber airbags (9) increase from a top of the folding airbag to a bottom of the folding airbag; wherein the top of the folding airbag is adjacent to the air cylinder grip (2).

3. The portable child anti-choking first aid equipment according to claim 2, comprising an air cylinder grip bracket (3) at the top of the folding airbag, wherein the air cylinder grip bracket (3) is equipped with the outgoing one-way valve (8), and the top of the folded airbag is connected to the air cylinder grip (2).

4. The portable child anti-choking first aid equipment according to claim 3, comprising an air cylinder bracket (5) at the bottom of the folded airbag, wherein the air cylinder bracket (5) is internally fitted with the inlet one-way valve (10), and the bottom of the folded airbag is connected to an air cylinder face shell (6).

5. The portable child anti-choking first aid equipment according to claim 4, wherein a bottom of the air cylinder face shell (6) is connected to the mask (1).

6. The portable child anti-choking first aid equipment according to claim 1, wherein a surface of the air cylinder grip (2) is provided with equally spaced exhaust holes (7).

* * * * *